US009237960B2

(12) United States Patent
Rasmussen et al.

(10) Patent No.: US 9,237,960 B2
(45) Date of Patent: Jan. 19, 2016

(54) APPARATUS FOR CURVING AN IMPLANTABLE MEDICAL DEVICE IN A LUMEN (75) Inventors: Erik E. Rasmussen, Slagelse (DK); Bent Oehlenschlaeger, Skensved (DK); Kim Moegelvang Jensen, Frederiksberg (DK)

(73) Assignee: Cook Medical Technologies LLC, Bloomington, IN (US)

(*) Notice: Subject to any disclaimer, the term of this patent is extended or adjusted under 35 U.S.C. 154(b) by 380 days.

(21) Appl. No.: 13/122,646

(22) PCT Filed: Oct. 9, 2009

(86) PCT No.: PCT/US2009/005545
§ 371 (c)(1),
(2), (4) Date: Jun. 1, 2011

(87) PCT Pub. No.: WO2010/042210
PCT Pub. Date: Apr. 15, 2010

(65) Prior Publication Data
US 2011/0276119 A1 Nov. 10, 2011

Related U.S. Application Data (60) Provisional application No. 61/195,760, filed on Oct. 10, 2008.

(51) Int. Cl.
A61F 2/06 (2013.01)
A61F 2/95 (2013.01)

(52) U.S. Cl.
CPC ............ A61F 2/95 (2013.01); A61F 2002/9505 (2013.01); A61F 2002/9511 (2013.01); A61F 2002/9517 (2013.01)

(58) Field of Classification Search
CPC ........................... A61F 2/95; A61F 2002/9505
USPC .................. 623/1.11–1.15, 1.2; 128/898, 899
See application file for complete search history.

(56) References Cited

U.S. PATENT DOCUMENTS 6,764,503 B1 7/2004 Ishimaru ...................... 623/1.11
2005/0143809 A1* 6/2005 Salahieh et al. ............. 623/2.11

(Continued)

FOREIGN PATENT DOCUMENTS

| WO | WO 2005/037361 A2 | 4/2005 | ............ A61M 29/00 |
| WO | WO 2006/037086 A1 | 4/2006 | ................ A61F 2/06 |
| WO | WO 2007/092276 A2 | 8/2007 | |
| WO | WO 2007/115483 A1 | 10/2007 | ................ A61F 2/84 |

OTHER PUBLICATIONS

International Search Report dated Dec. 10, 2009, issued in International Application No. PCT/US2009/005545, 8 pages.

Primary Examiner — Katherine Rodjom
(74) Attorney, Agent, or Firm — Brinks Gilson & Lione (57) ABSTRACT An introducer assembly (100) including at its distal end a dilator tip (20) and an inner catheter for supporting an implantable medical device (1) for deployment, is provided with a plurality of strut elements (102, 202) extending from the dilator tip (20) to the proximal end of the medical device (1). The strut elements (102, 202) act to apply both a pulling and a pushing force against the proximal end of the medical device (1), having the effect of assisting in the correct positioning of the proximal end of the medical device in a patient's lumen, particularly where this is curved such as with the aortic arch. The strut elements (102, 202) form part of the introducer assembly and are removed from the patient following the deployment procedure. The device avoids the need for bare stents at the end of a stent graft.

17 Claims, 6 Drawing Sheets

(56) References Cited

U.S. PATENT DOCUMENTS

| | | | |
|---|---|---|---|
| 2006/0155366 A1* | 7/2006 | LaDuca et al. | 623/1.23 |
| 2007/0198078 A1* | 8/2007 | Berra et al. | 623/1.12 |
| 2009/0099640 A1* | 4/2009 | Weng | 623/1.11 |
| 2009/0192585 A1 | 7/2009 | Bloom et al. | 623/1.11 |

* cited by examiner

APPARATUS FOR CURVING AN IMPLANTABLE MEDICAL DEVICE IN A LUMEN

CROSS REFERENCE TO RELATED APPLICATIONS

This application is the National State of International Application No. PCT/US2009/005545, filed Oct. 9, 2009, which claims the benefit of U.S. Provisional Application No. 61/195,760, filed Oct. 10, 2008, each of which is incorporated herein by reference in its entirety.

TECHNICAL FIELD

The present invention relates to apparatus for and a method of curving an implantable medical device, such as a stent or stent graft, in a lumen of a patient, particularly into a highly curved lumen such as the aortic arch and into locations which provide little room for error in the placement of the device, such as lumens having short necks of healthy vascular wall.

BACKGROUND ART

Implantable medical devices for the repair of vascular defects, including for example vascular aneurysms, are well known in the art. A common device for treatment of such a medical condition is a stent-graft.

Medical devices of this type are typically deployed endoluminally through a vein or artery adjacent a surface of a patient, aortic devices, for example, being commonly fed through the femoral artery. A generally accepted method of deployment involves the location of a guide wire along the path to be followed by the introducer assembly, up to the site in the vasculature to be treated. Once the guide wire is in place, a series of catheters is advanced along the guide wire, finally with the introduction of a catheter assembly which carries the stent or stent-graft to be fitted. The catheters have sufficient trackability to follow the guide wire along the curves and turns of the patient's vasculature and some can also curve sufficiently so as to be able to fit a stent-graft, for example, into a highly curved vessel such as the aortic arch.

Even though such a procedure is possible into the aortic arch, it is mired in difficulties as a result of the tight curvature of the aorta in this location. One such difficulty arises in connection with the proximal end of the stent-graft, which is liable to be incorrectly fitted such that it incompletely seals around the inner wall of the aorta as a result of the curvature imparted to the stent-graft. This can lead to leakage of blood around the outside of the stent-graft and thus a less than effective treatment. Furthermore, as a result of the non-optimal placement of the stent-graft using known procedures, it is necessary to have a reasonable length of healthy vascular wall in order to provide a seal around the proximal end of the stent-graft. This limits the application of such stent-grafts, in particular for the treatment of aneurysms close to a branch vessel and to conditions where there is at least a certain length of healthy vessel wall tissue, thus making the procedure not available to treat a reasonable proportion of medical cases.

In addition, in some instances at least, a part of the proximal end of the stent-graft can remain loosely located in the vessel, leading to premature fatigue failure as well as thrombus effects.

Attempts have been made to resolve these difficulties. For instance, in the applicant's U.S. Pat. No. 6,974,471, mechanisms are described for imparting a curvature to the stent-graft at the moment of its deployment.

Another example, disclosed in US-2006/155366, applies a curve to the introducer assembly in order to impart a curvature to the stent graft in order to place the latter in a curved lumen.

The deployment of stent-grafts and other devices, particularly in the aortic arch, in lumens having short necks of healthy vascular wall and other difficult pathologies also requires very precise placement of the device to ensure a good coupling to healthy tissue and in particular a coupling which has longevity and which provides a fluid-tight seal with the vessel wall. Prior art systems do allow for a certain amount of coarse re-positioning of the device. However, if the device is not fitted precisely in the correct location, the procedure may need to be repeated, for example by withdrawing the device back into its delivery introducer (where this is possible) and starting the deployment operation afresh. Repeating the procedure increases operating time, trauma to the patient and still does not guarantee a successful outcome. In some instances, it is necessary to abort the procedure.

Prior art introducer systems include wire tie elements able to pull the proximal end of the stent graft in the direction of the introducer. This does not, however, always provide a mechanism for ensuring correct positioning of the proximal end of the stent graft in a lumen, particularly in cases where the lumen is particularly curved.

Problems can also arise with the correct placement and orientation of a stent graft in other lumens or regions of the aorta of a patient and in order to ensure correct placement stent grafts are often provided with a stent ring which extends beyond the end of the graft material, often being called a bare stent. Such a bare stent typically plays no part in closing off blood supply to a lumen or part thereof, as does a graft covered stent, and normally only serves to support the end of the graft material correctly in the lumen.

While such bare stents can achieve the intended function efficiently, they can be the cause of other problems. For example, they require a length of suitable lumen against which to press. They can also induce stenosis or restenosis in the location in which they are fitted.

DISCLOSURE OF THE INVENTION

The present invention seeks to provide an improved system for and method of fitting an implantable medical device, such as a stent-graft, to a patient.

According to an aspect of the present invention, there is provided an introducer assembly for fitting an implantable medical device into a lumen of a patient, the implantable medical device being provided with a proximal end and a distal end; the introducer assembly being provided with a flexible carrier element for carrying a said implantable medical device, the carrier element including a distal end at which the implantable medical device is in use located, and a plurality of strut elements coupled at the distal end of the carrier element and operable to couple the distal end of the carrier element to the proximal end of the implantable medical device, wherein the plurality of strut elements are able to provide pulling and pushing forces against the proximal end of the implantable medical device during deployment thereof.

The provision of strut elements which can pull and push the proximal end of the stent graft can generate a more effective positioning action and thus better location of a stent graft in the lumen of a patient. In particular, when a stent graft or other device is located in a curved part of a lumen, those portions of the implant which are at the outside of the curve will tend to drag behind those parts at the inside of the curve, partly as a result of the tendency of the device to retain its non-curved condition and in part because there is less extent of lumen wall at the inside of the curve compared to the extent of lumen wall at the outside of the curve. The strut elements can therefore pull those portions of the implantable medical device at the outside of the curve forwards and can push those portions of the implantable medical device at the inside of the curve backwards. The latter feature can ensure that the proximal end of the implantable medical device will not extend beyond the inner curve wall and thus not suffer the problems of an incomplete seal in this zone, as can occur with prior art devices.

The strut elements, being part of the introducer assembly, can be used only during the deployment operation and thus need not form part of the medical device itself. This can avoid the need for the use of bare stents since once the stent graft has been properly located in the lumen, it is normally no longer necessary to have bare stents to hold the latter in place. Thus, problems which can be experienced with bare stents can be avoided.

Advantageously, each strut element is able to provide both a pulling and a pushing action on the implantable medical device, in dependence upon what is required during deployment. The provision of such double acting struts means that the introducer assembly will correctly position the proximal end of a stent graft in a lumen irrespective of the orientation of the stent graft and the introducer in a vessel. In other words, it is not necessary for either the device or the introducer to be rotationally aligned in the lumen of a patient for the proximal end of the device to be correctly positioned. This can be particularly advantageous in instances of deployment of a stent graft with no side branches, fenestrations and the like which require a specific alignment. Moreover, such struts can be of a similar or identical construction, simplifying manufacture and assembly.

In another embodiment, the plurality of strut elements includes at least one strut able to provide a pulling action and at least one strut element able to provide a pushing action. In some implementations, the orientation of a stent graft in a vessel during its deployment is predetermined, for example in the case of a stent graft which requires a particular orientation in the lumen of a patient, such as one with side branches or fenestrations. In such a case, the configuration of the lumen and thus of the deployment operation will be known with sufficient accuracy that it will be known which parts of the proximal end of the stent graft will need to be pulled into position and which will need to be pushed to the correct position. Thus, the introducer can be designed with specific strut elements able to affect one of a pulling or a pushing action, as required around the radial directions of the stent graft.

In the preferred embodiment, there are provided at least three strut elements arranged radially around the carrier element. Most preferably, there are provided at least four, in some cases five or six.

It will be appreciated that the arrangements of struts disclosed herein can provide orientation of a medical device during the deployment operation and can also be used to orient the medical device on the introducer itself as the struts can be used to provide orientation of the device to the introducer in a manner which is more reliable and efficient than prior art devices in which the introducer, at least the distal end thereof, provides no radially oriented features for assisting in the orientation of the device carried thereon.

Each strut element is preferably formed so as to be able to extend radially outwardly of the carrier element in a distal or downstream direction. Each strut element is preferably provided with a mechanism to urge the strut element towards a compressed configuration adjacent the carrier element. Thus, each strut element can extend outwardly to support and position a medical device as it expands off the carrier element during deployment and can be retracted towards the carrier element for removal of the introducer assembly after deployment of the medical device.

In the preferred embodiment, each strut element is formed as a length of wire having a distal end fixed to the carrier element. The distal end of the strut element may be permanently fixed to the carrier element or may be removable therefrom, for example for removal of the strut element from a patient following deployment.

In one embodiment, the mechanism for urging the strut element towards the carrier element acts to pull a proximal end of the strut element proximally, in other words backwards towards the external manipulation end of the introducer.

Advantageously, the mechanism is formed as an extension of the strut elements that is as a continuation of the wire forming the strut elements. This is considered to be the most convenient and reliable mechanism for pulling the strut elements back towards the carrier element and away from the medical device after its deployment.

The proximal ends of the strut elements are preferably tied to the medical device. This ensures that the strut elements are properly aligned to the medical device so that they can act thereupon and can also enable them to apply both a pushing as well as a pulling force on the proximal end of the medical device.

In the preferred embodiment, there is provided an engagement assembly operable to couple the struts releasably to the proximal end of a medical device. Advantageously, the engagement assembly includes a tie element operable to tie a respective strut to the proximal end of a medical device, and a release wire operable to release the strut from the tie element. The tie element in one embodiment includes a loop of suture thread sutured to the proximal end of a medical device, the release wire being operable to tie the loop of suture thread to its associated strut element.

In an embodiment, the struts are provided with first and second loops of wire through which the release wire tie element is able to slide, the release wire including an enlarged distal end able to pass through the first loop of wire but not through the second, wherein the loop of suture thread is held between the first and second wire loops by the release wire, thereby being tied to its associated strut, and releasable therefrom upon withdrawal of the release wire from the first wire loop. For this purpose, the second loop preferably provides a smaller opening relative to the first loop.

According to another aspect of the present invention, there is provided an assembly including an introducer as specified herein and an implantable medical device.

It is to be understood that although the various embodiments described below make reference to an introducer for deploying a stent graft, the teachings herein can be used for the deployment of a variety of medical devices and in particular any medical device to be deployed endoluminally. Examples include stent grafts, stents, vena cava filters, occlusion devices and so on.

BRIEF DESCRIPTION OF THE DRAWINGS

Embodiments of the present invention are described below, by way of example only, with reference to the accompanying drawings, in which.

DESCRIPTION OF THE PREFERRED EMBODIMENTS

For the purposes of this disclosure, when used in connection with description of a stent-graft or other implantable medical device, the term "proximal" refers to a part or position closest to the heart, that is upstream in the direction of blood flow, while the term "distal" refers to a part or position furthest from the heart. On the other hand, when used in connection with an introducer assembly the term "proximal" refers to a position or part closest to the surgeon and typically kept outside the patient, while the term "distal" refers to a position or part furthest from the surgeon and in practice furthest into a patient during a deployment procedure.

Figure 1:
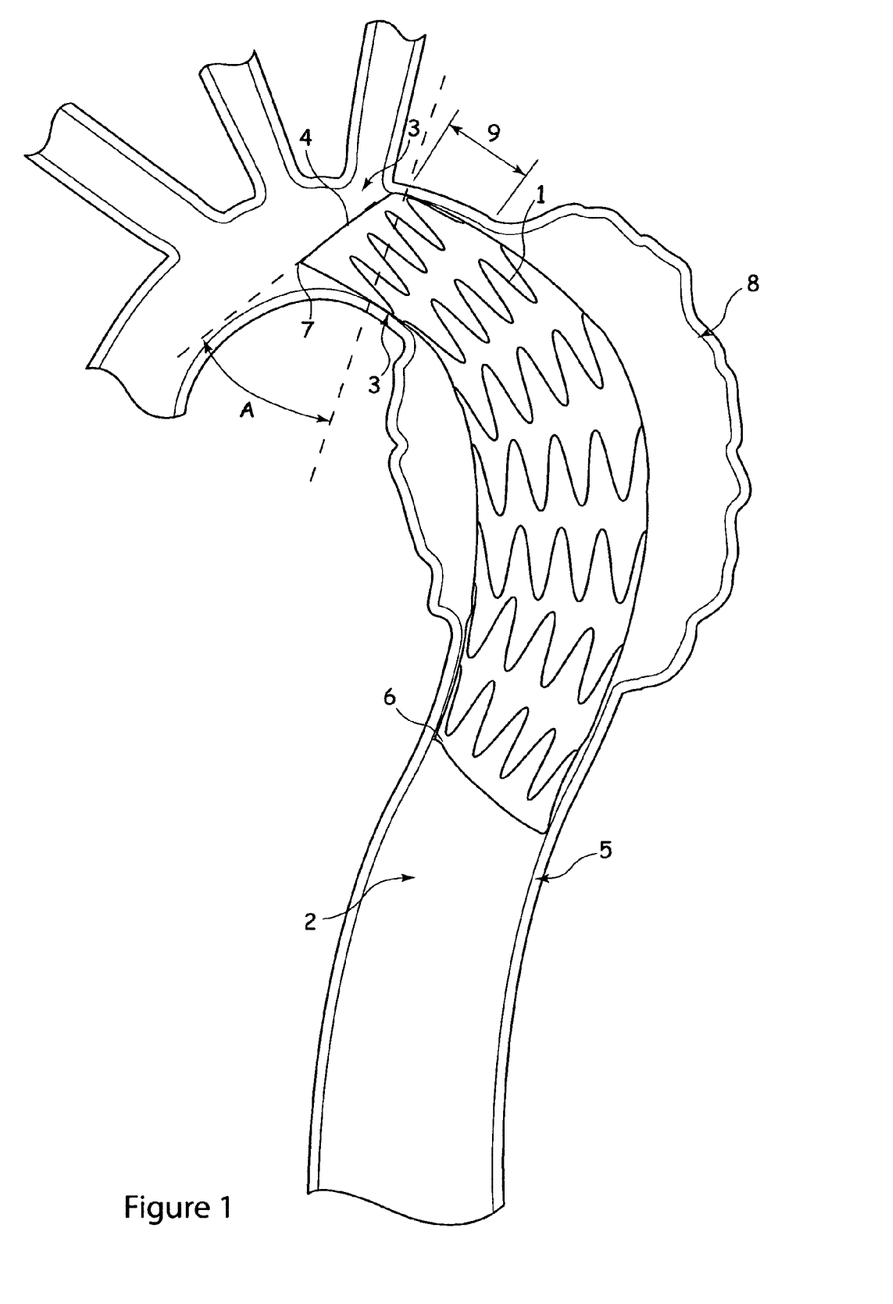
FIG. 1 shows an example of stent-graft deployed in the aortic arch by a conventional introducer system.

Referring to FIG. 1, there is shown an example of deployment of a stent-graft 1 within the aorta 2 of a patient for the treatment of, for example, an aneurysm 8. In this particular example, the stent-graft extends part-way into the aortic arch 3 at its proximal end 4, down to the thoracic aorta 5 at its distal end 6. The curvature of the aortic arch 3, coupled with use of a conventional introducer system which follows the arch 3 by being bent thereby, can cause the proximal end 4 of the stent-graft 1 to be located incorrectly, that is not to have its opening perpendicular with the vessel at that position. As a result, the inner side 7 of the stent-graft 1 stands proud of the vessel wall, being spaced therefrom. In particular, the proximal end 4 of the stent graft will typically tend to lie at an angle A which deviates from the perpendicular line B. The resultant gap between the inner side 7 and the aortic wall provides a path for leakage of blood and thus an incomplete seal, which can lead to failure of the stent-graft in achieving its intended function. In practice, such imprecise deployment results in it being necessary to have a relatively long neck 9 to achieve a reliable seal between the stent-graft 1 and the vessel wall as well as limiting the application of such implantable medical devices to areas lumens which have no more than a certain curvature, in some cases thus excluding the aortic arch. Thus, medical conditions which do not have a sufficient length of adequate neck 9, that is of healthy vessel wall, or which have too great a curvature cannot at present be treated.

In addition to these problems, the end 7 of the stent-graft tends to flap in the force of blood flow, leading to possible stent-graft collapse, fatigue wear and possibly rupture, as well as to thrombus formation.

Figure 2:
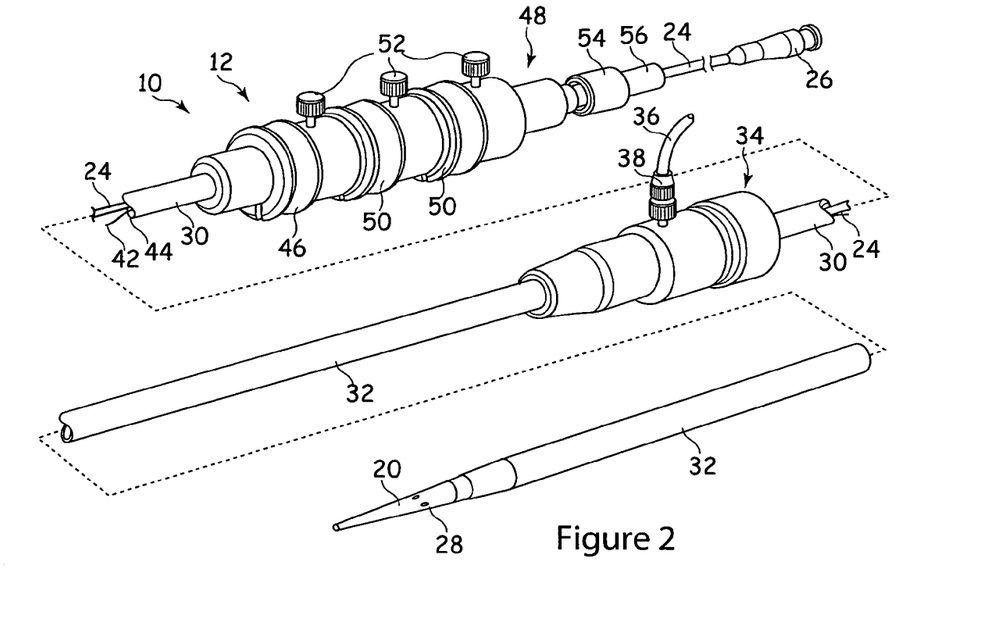
FIGS. 2 and 3 are perspective views of an example of introducer system which can incorporate the strut system taught herein.
Figure 3:
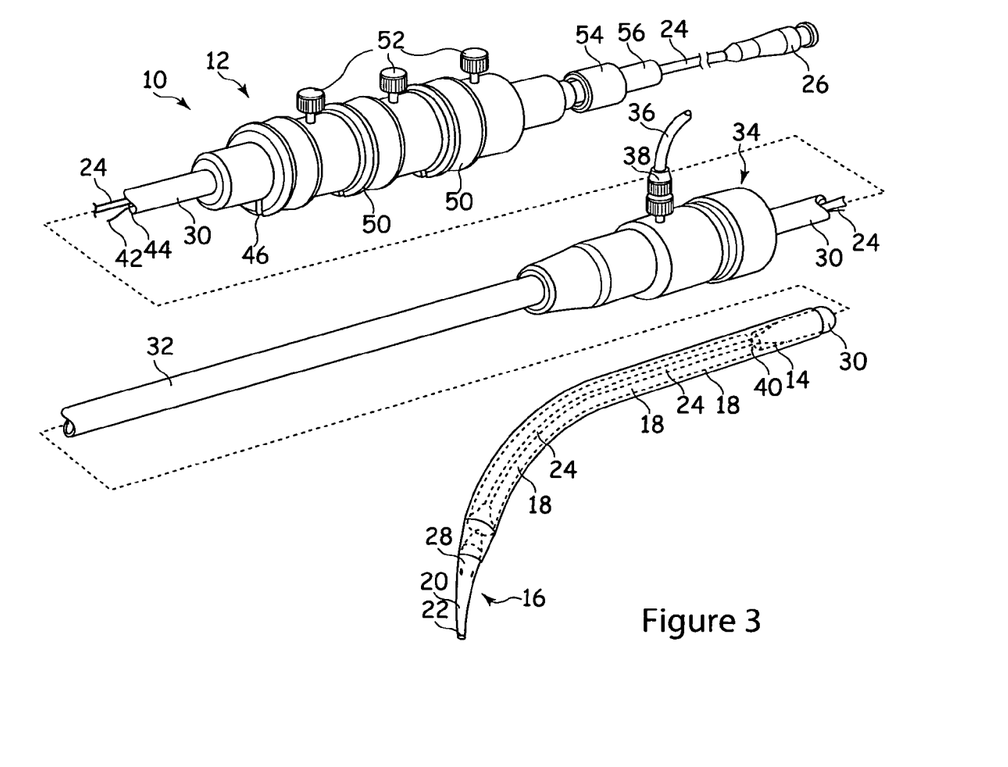

Referring now to FIGS. 2 and 3, there is shown an example of introducer of the type used in the deployment of stent-grafts of the form shown in FIG. 1. The introducer 10 includes an external manipulation section 12, a distal attachment region 14 and a proximal attachment region 16. The distal attachment region 14 and the proximal attachment region 16 secure the distal and proximal ends of the implant 18, respectively. During the medical procedure to deploy the implant 18, the distal and proximal attachment regions 14 and 16 will travel through the patient's lumen to a desired deployment site. The external manipulation section 12, which is acted upon by a surgeon to manipulate the introducer, remains outside of the patient throughout the procedure.

The proximal attachment region 16 of the introducer 10 includes a dilator tip 20, which is typically provided with a bore 22 therein for receiving a guide wire 25 of conventional type. The longitudinal bore 22 also provides a channel for the introduction of medical reagents. For example, it may be desirable to supply a contrast agent to allow angiography to be performed during placement and deployment phases of the medical procedure.

A guide wire catheter 24, conventionally made from a flexible thin walled metal tube, is fastened to the dilator tip 20. The guide wire catheter 24 is flexible so that the introducer 10 can be advanced along a relatively tortuous vessel, such as a femoral artery, and so that the distal attachment region 14 can be longitudinally and rotationally manipulated. The guide wire catheter 24 extends through the introducer 10 to the manipulation section 12, terminating at a connection device 26, in conventional manner.

The connection device 26 is designed to accept a syringe to facilitate the introduction of reagents into the inner catheter 24. The guide wire catheter 24 is in fluid communication with apertures 28 in the flexible dilator tip 20. Therefore, reagents introduced into connection device 26 will flow to and emanate from the apertures 28.

A pusher sheath or rod 30 (hereinafter referred to as a pusher member), typically made from a plastics material, is mounted coaxial with and radially outside of the guide wire catheter 24. The pusher member 30 is "thick walled", that is the thickness of its wall is preferably several times greater than that of the guide wire catheter 24.

A sheath 32 extends coaxially over and radially outside of the pusher member 30. The pusher member 30 and the sheath 32 extend distally to the manipulation region 12.

The implant 18, which may be a stent, a stent-graft or any other implant or prosthesis deliverable by this device 10, is retained in a compressed condition by the sheath 32. The sheath 32 extends distally to a sheath manipulator and haemostatic sealing unit 34 of the external manipulation section 12. The haemostatic sealing unit 34 includes a haemostatic seal (not shown) and a side tube 36 held to the unit 34 by a conventional luer lock 38.

The sheath manipulator and haemostatic sealing unit 34 also includes a clamping collar (not shown) that clamps the sheath 32 to the haemostatic seal and a silicone seal ring (not shown) that forms a haemostatic seal around the pusher rod 30. The side tube 38 facilitates the introduction of medical fluids between the pusher rod 30 and the sheath 32. Saline solution is typically used.

During assembly of the introducer 10, the sheath 32 is advanced over the proximal end of the dilator tip 20 of the proximal attachment region 16 while the implant 18 is held in a compressed state by an external force. A suitable distal attachment (retention) section (not visible in this view) is coupled to the pusher rod 30 and retains a distal end 40 of the prosthesis 18 during the procedure. The distal end of the prosthesis 18 is provided with a loop (not shown) through which a distal trigger wire 42 extends. The distal wire also extends through an aperture (not shown in FIGS. 1 and 2) in the distal attachment section 40 into an annular region 44 between the inner catheter 24 and the pusher rod 30. The distal trigger wire 42 extends through the annular space 44 to the manipulation region 12 and exits the annular space 44 at a distal wire release mechanism 46.

A proximal portion of the external manipulation section 12 includes at least one release wire actuation section 50 mounted on a body 48, in turn mounted onto the pusher member 30. The guide wire catheter 24 passes through the body 48. The distal wire release mechanism 46 and the proximal wire release mechanism 50 are mounted for slidable movement on the body 48.

The positioning of the proximal and distal wire release mechanisms 46 and 50 is such that the proximal wire release mechanism 46 must be moved before the distal wire release mechanism or mechanisms 50 can be moved. Therefore, the distal end of the implant 18 cannot be released until a self-expanding zigzag stent thereof has been released. Clamping screws 52 prevent inadvertent early release of the prosthesis 18. A haemostatic seal (not shown) is included so that the release wires can extend out through the body 48 without unnecessary blood loss during the medical procedure.

A proximal portion of the external manipulation section 12 includes a pin vise 54 mounted onto the proximal end of the body 48. The pin vise 54 has a screw cap 56. When screwed in, vise jaws (not shown) of the pin vise 54 clamp against or engage the guide wire catheter 24. When the vise jaws are engaged, the guide wire catheter 24 can only move with the body 48 and hence it can only move with the pusher member 30. With the screw cap 56 tightened, the entire assembly can be moved together as one piece.

Once the introducer assembly 12 is in the desired deployment position, the sheath 32 is withdrawn to just proximal of the distal attachment section 14. This action releases the middle portion of the implant 18, in this example a stent or stent-graft, so that it can expand radially. Consequently, the stent or stent-graft 18 can still be rotated or lengthened or shortened for accurate positioning. The proximal end self-expanding stent however, is still retained at the dilator tip 16 by means of the release wires. Also, the distal end of the stent or stent-graft 18 will still retained within the sheath 32.

Next, the pin vise 54 is released to allow small movements of the guide wire catheter 24 with respect to the pusher rod 30 to allow the stent or stent-graft 18 to be lengthened, shortened, rotated or compressed for accurate placement in the desired location within the lumen. X-ray opaque markers (not shown) may be placed along the stent or stent-graft 18 to assist with placement of the prosthesis.

When the proximal end of the stent or stent-graft 18 is in place, the proximal trigger wire is withdrawn by distal movement of the proximal wire release mechanism. The proximal wire release mechanism 50 and the proximal trigger wire can be completely removed by passing the proximal wire release mechanism 50 over the pin vise 54, the screw cap 56 and the connection unit 26.

Next, the screw cap 56 of the pin vise 54 is loosened, after which the inner catheter 24 can be pushed in a proximal direction to move the dilator tip 20 in a proximal direction. When the dilator tip 20 no longer surrounds the end of the stent or stent-graft 18, it expands to engage the lumen walls of the patient. From this stage on, the proximal end of the stent or stent-graft 18 cannot be moved again.

Once the proximal end of the stent or stent-graft 18 is anchored, the sheath 32 is withdrawn distally of the distal attachment section 14, which withdrawal allows the distal end of the stent or stent-graft 18 to expand. At this point, the distal end of the stent or stent-graft 18 may still be repositioned as needed.

As will be apparent in particular from FIG. 1, the distal end of the introducer is flexible, so as to be able to follow a tortuous path of a patient's vasculature, as well as in some applications to locate a stent-graft in a curved portion of a lumen such as the aortic arch. The distal end curves, however, by being pulled into this configuration as a result of curving of the guide wire, which is itself urged into a curved shape by the curvature of the lumen. As a result of this, the distal end of the introducer tends to follow the outside of any curve. When deployment occurs in such a situation, as it does in the aortic arch for example, the stent-graft can become improperly located, as in the example of FIG. 1.

Figure 4:
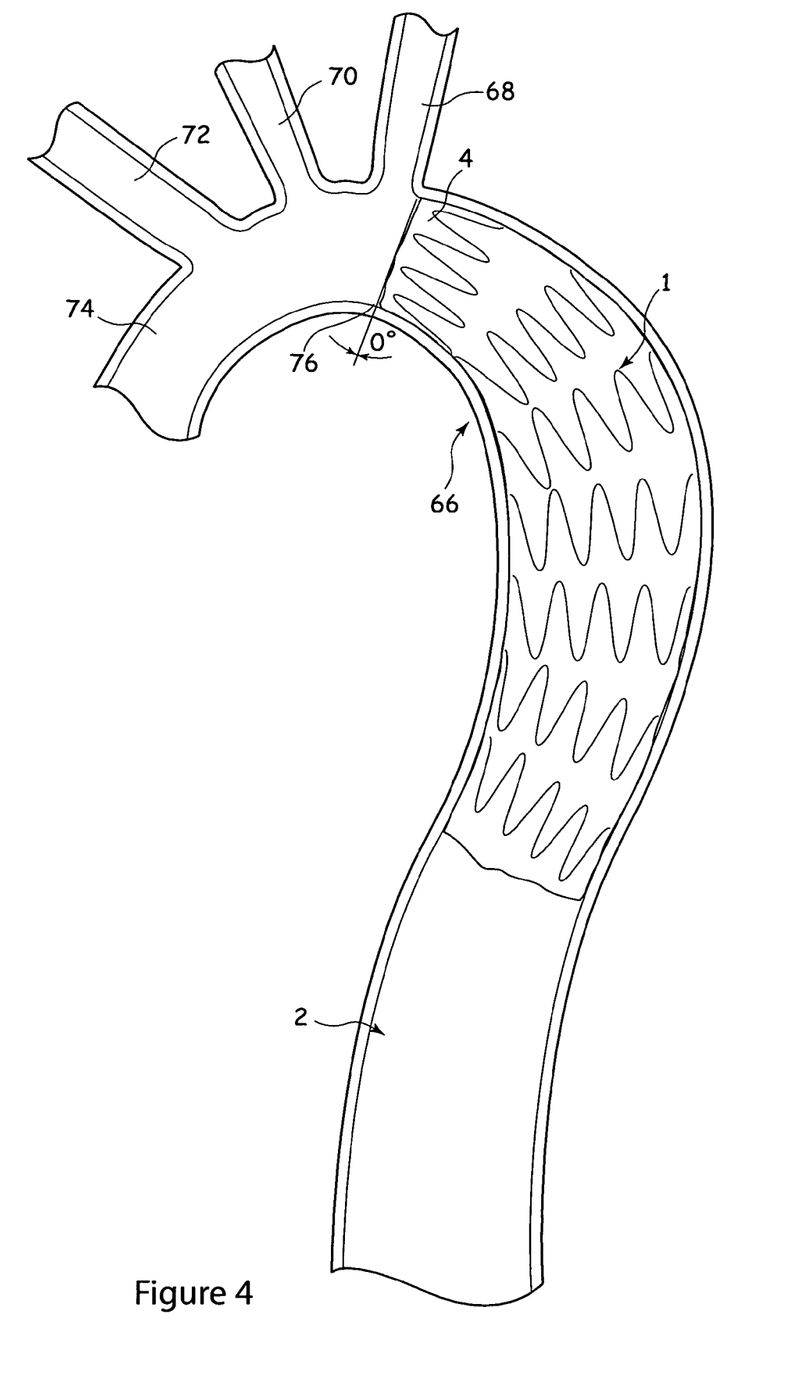
FIG. 4 is a view similar to that of FIG. 1 showing the ideal placement of a stent-graft within the aortic arch.

The optimal configuration for the stent-graft is shown in FIG. 4. As can be seen, the stent-graft 1 is properly deployed in an aorta 2 of a patient. The proximal end 4 of the stent-graft 1 is positioned in the aortic arch 66, just short of the left subclavian artery 68, in this example, although in some circumstances may extend to beyond the left subclavian artery 68, or even beyond the left common carotid artery 70 and the brachiocephalic artery 72 and into the ascending aorta 74. Fenestrated or branched stent-grafts for such applications are known in the art.

It will be noted that the proximal end 4 lies correctly in FIG. 4, so as to be substantially perpendicular to the vessel, that is such that the opening of the device is perpendicular to the vessel wall and the graft tubing at the distal end is properly aligned with the walls of the vessel. In this orientation, the device properly seals to the vessel wall around all of its circumference, including at the radially internal side 76, leaving no gap for blood leakage.

Precise and reliable placement of the proximal end 4 of the stent-graft 1 allows this to be fitted in a much shorter neck length of vessel wall compared to the less reliable prior art systems.

The present invention seeks to address the problems encountered with prior art introducer systems in a way which can enhance the fitting of the stent-graft into a lumen, particularly at the aortic arch and other highly curved regions of vasculature. Although the preferred embodiments disclosed herein relate to a stent graft it will be appreciated that the teachings herein are not limited to the deployment of a stent graft but are equally applicable to a large range of implantable medical devices including stents, vena cava filters, occlusion devices and so on.

Figure 5:
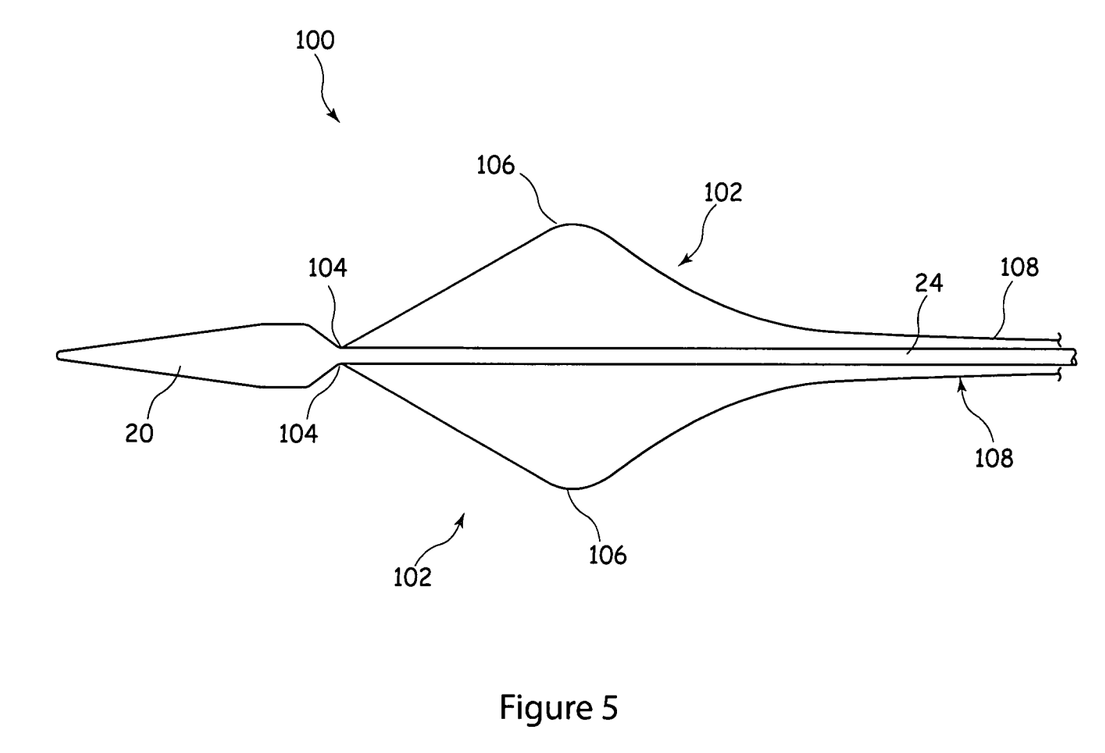
FIG. 5 is a side elevational view in schematic form of the principal components of the preferred embodiment of introducer assembly.

Referring now to FIG. 5, there is shown in schematic form the distal end of a preferred embodiment of introducer assembly incorporating a medical device holding device of the type taught herein. In this embodiment, the device includes a plurality of strut elements 102.

More specifically, FIG. 5 shows the distal end of the introducer assembly and in particular the dilator tip 20 and guide wire catheter 24. A stent graft 1 or other implantable medical device is typically carried on the introducer at the portion of the guide wire catheter 24 visible in FIG. 5.

Extending at or proximate the distal end of the dilator tip 20, that is around the region of the junction between the dilator tip 20 and the inner catheter 24, there is provided a plurality of strut elements 102, shown schematically in FIG. 5. Advantageously, the distal ends 104 of the strut elements 102 are fixed to or into the dilator tip 20, which provides a convenient fixing element as a result of its volume and structure. In other embodiments, the distal ends 104 of the strut elements 102 could be fitted to or into the inner catheter 24 or at the interstice between the dilator tip 20 and the inner catheter 24.

FIG. 5 shows two strut elements 102 extending from the proximal end of the dilator tip 20 and arranged substantially radially opposite one another. It is envisaged that two strut elements 102 is the minimum number of such elements which would be provided for an introducer, although it is not excluded that an introducer could be provided with a single strut element 102 oriented in use on the inside of the curve of the introducer in a patient's lumen, there being provided another element for pulling the part of a device to be implanted at the outside of the curve, for example a thread or wire.

In the preferred embodiment, there are provided more than two strut elements 102, such as three, four or preferably more, such as six or eight. It is preferred that the strut elements 102 are substantially equidistally spaced circumferentially around dilator tip 20 and inner catheter 24 as this gives to the introducer a substantially symmetrical characteristic which results in it being equally effective irrespective of its rotational orientation in patient's vessel. Of course, in some instances, it my be preferable to have different concentrations of strut elements 102 radially around the inner catheter 24 in dependence upon, for example, the medical devices to be deployed or the particular physiology of the patient's lumens at the location of deployment.

As can be seen in FIG. 5, the strut elements 102 are substantially straight from their distal ends 104 to an apex 106. The apex 106 is intended to be at a radial distance from the inner catheter 24 equivalent to the substantially fully deployed size of the medical device carried on the catheter. In other words, the apices 106 of the strut elements 102 preferably extend in a radial direction outwardly enough in order to ensure proper positioning of the proximal end of a medical device (as described below in detail) against the walls of the patient's lumen and thus in practice would encompass a diameter at least as large as and preferably greater than the diameter of the lumen at the point of deployment.

From the apices 106, the strut elements 102 continue in a proximal direction of the introducer 100 by way of tail elements or wires 108. In practice, the wires 108 extend to an external manipulation section of the introducer 100 and have the function of controlling the configuration of the strut elements 102 and in particular the amount by which the apices 106 extend out from the inner catheter 24.

Figures 6, 7:
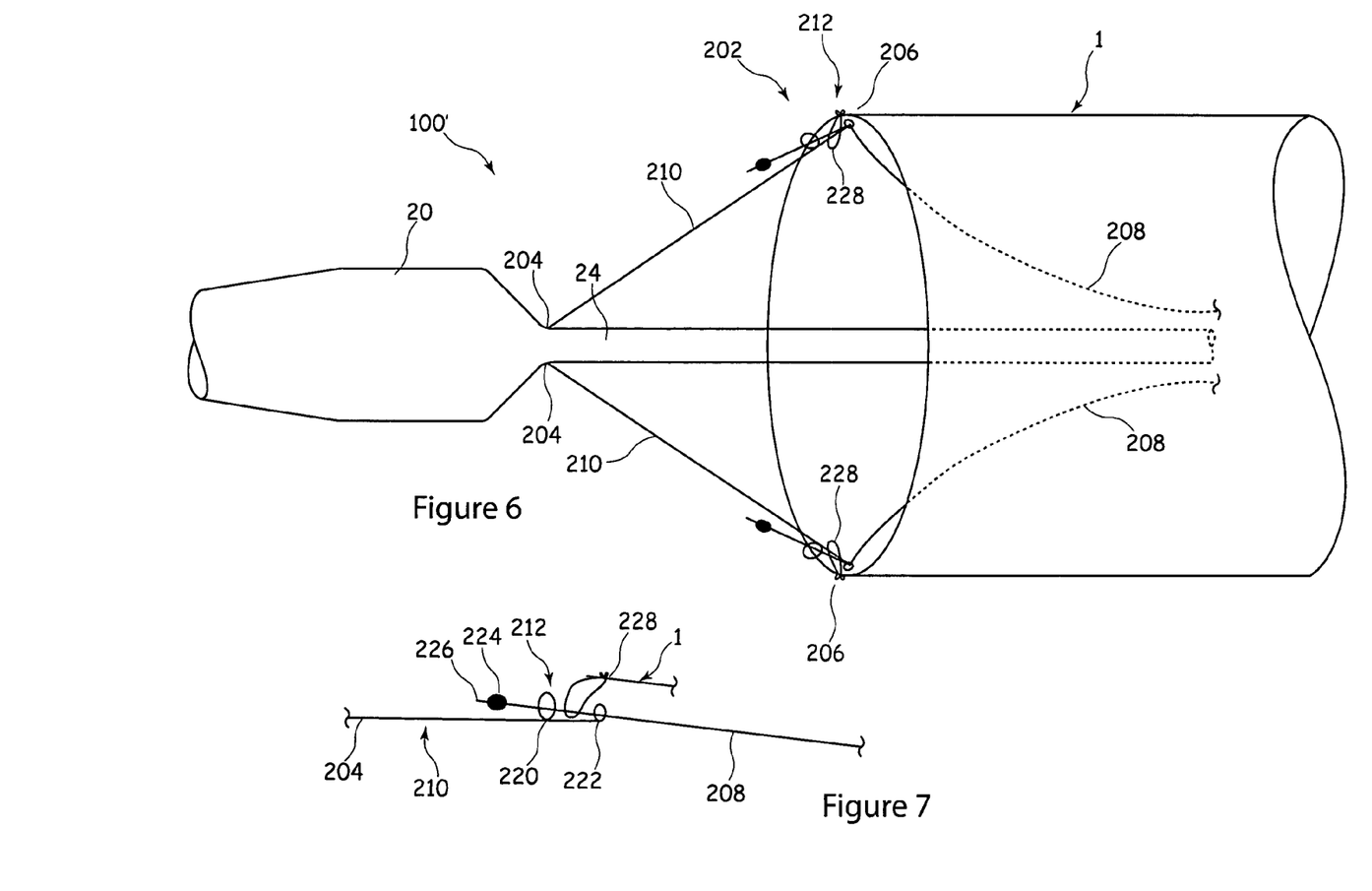
FIG. 6 is a side elevational and enlarged view of a part of the distal end of the introducer assembly of FIG. 5, with a stent graft fitted thereto.
FIG. 7 is a schematic diagram of a part of a strut and release wire configuration of the introducer of FIG. 6.

Referring now to FIGS. 6 and 7, there is shown a preferred embodiment of strut assembly 202 having the general features of the strut assembly 102 shown in schematic form in FIG. 5.

The strut assembly 202 shown in FIGS. 6 and 7 has two principal components, namely the struts 210 themselves and separate tails or wires 208 coupled thereto by a coupling arrangement 212 described in detail below. The tails or wires 208 are equivalent to the wires 108 of the simple embodiment of FIG. 5 and extend to a proximal end of the introducer, typically to an external manipulation device operable by the surgeon or the clinician.

The strut elements 210, which are generally straight, extend radially outwardly to an apex 206 which, as can be seen, extends radially outwardly at least up to the diameter of the medical device, in this case stent graft 1, when deployed.

Each strut element 210 is coupled to a respective tail or wire 208 by coupling arrangements shown in better detail in FIG. 7. As can be seen, the distal end of each strut 204 is provided with first and second spaced rings 220, 222 which are fixed to the strut elements 204, by welding, by being formed integrally therewith or by any suitable method. The first ring 220 is of a larger internal diameter then the second ring 222, the latter being at the extremity or close to the extremity of the strut element 210. The tail or wire 208 is provided with an enlarged end 224 at or adjacent its proximal end 226. The enlarged head 224, which may be a knot, a ball of metal metallic material or any other suitable element, is sized so as to be able to pass through the first ring 220 but is sufficiently large that it cannot pass through the smaller ring 222.

The proximal end of the stent graft 1 is provided with a plurality of loops of thread 228 sutured, in the preferred embodiment, to the graft material of the stent graft 1. These loops of suture thread wrap around a respective wire 208 between the two ring 220 and 222 of the stent strut 210.

While the wires 208 pass through both rings 220, 222 of the strut 210, the suture loop 228 and thus the part of the medical device 1 attached to the suture loop 228 remains tied to the strut 210. The location of the rings 220, 222 ensures that the suture thread 228 will move substantially in correspondence with any movement of the respective strut 210 and this in turn will cause similar movement of the respective portion of the medical device 1 attached thereto. More particularly, if the strut 210 is moved in a distal direction, to the left of the views of FIGS. 6 and 7, the suture thread 228 and thus its respective part of the stent graft 1, will also move in a distal direction, that is left in the views of FIGS. 6 and 7 as a result of being constrained by the ring 222. On the other hand, when the strut 210 moves relatively in a proximal direction, that is to the right of the views of FIGS. 6 and 7, the suture loop 228 will be constrained for movement by the first ring 220 and will thus move substantially in accordance with the movement of the strut 210, as a result of the relative rigidity of the strut 210. Thus, in this condition, when the strut 210 is moved in a distal direction (to the left of the drawings of FIGS. 6 and 7) there will be an effect of pulling the associated suture loop 228 and the respective part of the proximal end of the medical device 1. On the other hand, when the strut 210 moves in a proximal direction, that is to the right of the views in FIGS. 6 and 7, the suture loop 228 will be constrained by the first ring 220 to be pulled in a proximal direction, thereby compressing the associated part of the proximal end of the medical device 1. Therefore, the proximal end of the medical device 1 can be pulled in extension or pushed in compression in dependence upon the movement of the strut 210.

Figure 8:
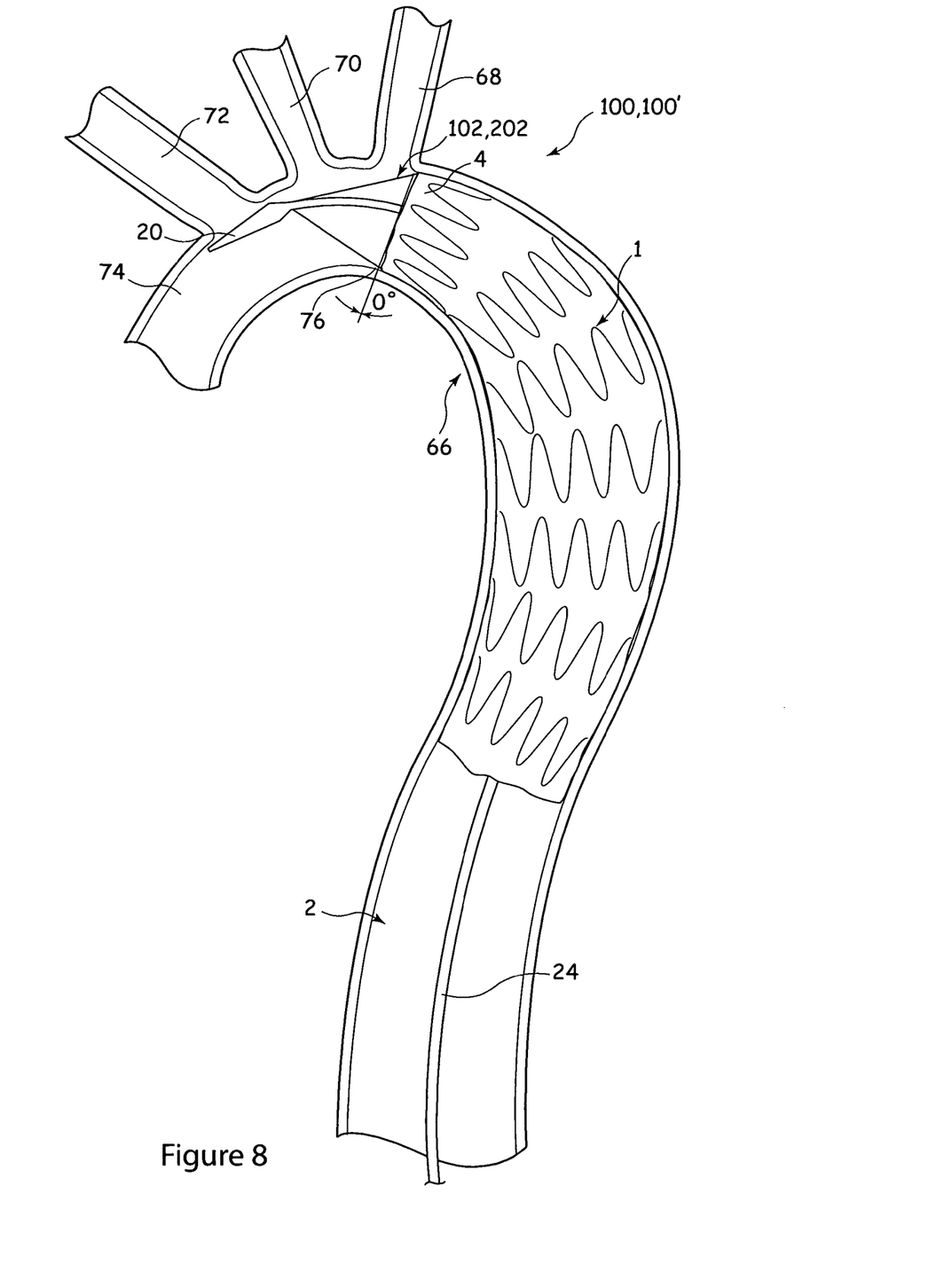
FIG. 8 is a schematic diagram of the introducer of FIGS. 5 and 6 in situ in a patient's artery during deployment of a stent graft.

Referring next to FIG. 8, those shown in schematic form the introducer 100, 100' in situ in a patient's lumen and in particular such that the distal end of the introducer is located in the aortic arch of a patient's aorta. The stent graft 1 is located just prior to the subclavian artery 68. During the deployment procedure, the dilator tip 20 is moved to a location further upstream than the subclavian artery 68 and the stent graft 1 released for extension by withdrawing the outer sheath 32 of the introducer and by releasing any restraining wires holding the stent graft in a compressed form on the inner catheter 24. During the deployment of the stent graft 1, its proximal end remains attached to the strut elements 102, 202, as can be seen in particular in FIG. 8. As a result of the attachment of the strut elements 102, 202 to the proximal end of the stent graft 1 and the relative stiffnesses of the strut elements 102, 202, they have the effect of pulling the regions of the stent graft 1 closest to the outside of the curve in an upstream direction while pulling those parts of the stent graft 1 on the inside of the curve in a downstream direction. More specifically, the strut elements 102, 202 ensure that the proximal end of the stent graft 1 remains substantially perpendicular to the direction of the inner catheter 24 and substantially perpendicular to the vessel wall, thereby to obtain a position of the proximal end of the stent graft 1 as close to the perpendicular of the vessel as can be achieved.

Referring again to FIGS. 6 and 7, once the stent graft 1 has been correctly deployed as shown in FIG. 8, the strut elements 102, 202 can be disengaged from the proximal end of the stent graft 1. In the embodiments of FIGS. 6 and 7, this can be achieved by releasing the suture loops 228 from the strut elements and thus from the introducer 100. This is achieved by pulling back on the tails or wires 208, in a proximal direction towards the external manipulation end of the introducer 100. When so pulled back, the enlarged head 224 of the wires or tails 208 will be withdrawn through the first ring 220 of the strut elements 210. As the enlarged head 224 is pulled through the first ring 220 it moves the wire 208 from between the two rings 220, 222 and thus allows the loop 228 to be released from its coupling to the strut elements 210 through the wires 208. Once the loops 228 are released from the strut elements 210, further pulling of the wires or tails 208 in a proximal direction of the introducer will have the effect of pulling the strut elements 210 back towards the inner catheter 24 and thus for pulling down the apices 206. The strut elements 210 can thus adopt a compressed profile in order to facilitate the withdrawal of the introducer from the patient.

It will be appreciated that FIGS. 6 and 7 show just one embodiment of a variety of possible solutions for tying the strut elements 210 temporarily to a stent graft 1 or other medical device to be deployed. Other systems, including cribs, breakable bonding, particular profiles formed into the wire of the strut elements 102 could equally be used.

It is preferred that the strut elements 102, 202 spring outwardly to the configuration shown in the drawings. This can be useful in ensuring correct positioning of the implantable medical device. This is, however, by no means essential and in other embodiments the strut elements 102, 202 could either be rotatable about their coupling to the distal end or even biased to the catheter 24.

The embodiments described above include strut elements 102, 202 which are able to provide both a pushing and a pulling action on the proximal end of a stent graft or other medical device to be deployed endoluminally in a patient. In other embodiments, some struts can be arranged to provide a pushing action while other struts may be arranged to provide a pulling action. An example is already given above and other examples could include some struts having characteristics, for instance, of the embodiment of FIGS. 6 and 7 and other struts having notches or other arrangements able to apply a pushing force against a part of the proximal end of a medical device to be deployed.

It will be appreciated that although the embodiments described above make use of an introducer having a dilator tip, such a tip is not essential for implementation of the principles taught herein. The feature of the strut elements could equally be applied to a tipless introducer, for instance.

The invention claimed is:

1. An introducer assembly for fitting an implantable medical device into a lumen of a patient, the implantable medical device being provided with a proximal end and a distal end; the introducer assembly comprising:
a flexible carrier element with the implantable medical device disposed thereon, the carrier element including a distal end, a nose cone directly connected to the flexible carrier element at the distal end of the flexible carrier element, and a distal portion upon which the implantable medical device is disposed proximal of the nose cone and over the flexible carrier element, the nose cone having a proximal end, and a plurality of strut elements fixedly connected to the proximal end of the nose cone or to the flexible carrier element adjacent the nose cone and coupling the carrier element to the proximal end of the implantable medical device,
wherein each of the plurality of strut elements is releasably connected to the proximal end of the implantable device and has sufficient rigidity to provide both a pulling force and a pushing force against the proximal end of the implantable medical device during deployment thereof to position different regions of the proximal end of the implantable medical device relative to one another in a distal direction and a proximal direction along a lumen of a patient, and
wherein each of the plurality of strut elements extends to a user end of the introducer assembly and each of the plurality of strut elements is individually movable to provide the pushing and pulling force against the proximal end of the implantable medical device.

2. The introducer assembly of claim 1, wherein each strut element is formed as a length of wire having a distal end fixed to the carrier element.

3. The introducer assembly of claim 2, wherein each strut element is extendable radially outwardly from the carrier element in the distal direction.

4. The introducer assembly of claim 3, wherein each strut element further comprises a mechanism to urge the strut element to move from a radially outward configuration towards a compressed configuration adjacent the carrier element.

5. The introducer assembly of claim 4, wherein the mechanism is configured to pull a proximal end of the strut element in the proximal direction.

6. The introducer assembly of claim 5, wherein the mechanism is formed as an extension of the strut elements.

7. The introducer assembly of claim 1, further comprising an engagement assembly operable to couple the strut elements releasably to the proximal end of the medical device.

8. The introducer assembly of claim 7, wherein the engagement assembly includes a tie element tying a respective strut element to the proximal end of the implantable medical device, and a release wire to release the strut element from the tie element.

9. The introducer assembly of claim 8, wherein the tie element includes a loop member attached to the proximal end of the implantable medical device, the release wire tying the loop member to an associated strut element.

10. The introducer assembly of claim 9, wherein the strut elements comprise first and second rings through which the release wire is slidable, the release wire including an enlarged distal end able to pass through the first ring but not the second ring, wherein the loop member is held between the first and second rings by the release wire, thereby being tied to the associated strut element, and releasable from the associated strut element upon withdrawal of the release wire from the first ring.

11. The introducer assembly of claim 1, wherein the plurality of strut elements comprises a pair of strut elements arranged radially around the carrier element, radially opposite from one another, so that the different regions of the proximal end are configured to be pulled in extension or pushed in compression in dependence upon the movement of the pair of strut elements.

12. An introducer system for fitting an implantable medical device into a curved lumen of a patient, comprising:
the implantable medical device having a first end and a second end; and
an introducer comprising a flexible carrier element disposed within and carrying the implantable medical device over the flexible carrier element, the flexible carrier element including a distal end having a nose cone attached to the distal end, a distal portion proximal of the nose cone at which the implantable medical device is located, and a plurality of substantially rigid strut elements fixedly connected to a proximal end of the nose cone or to the flexible carrier element adjacent the nose cone and arranged radially around the carrier element, the strut elements releasably coupling the distal end of the carrier element to the first end of the implantable medical device, wherein each of the strut elements has sufficient rigidity to provide both pulling and pushing forces against the first end of the implantable medical device during deployment thereof for relative placement of the first end in a distal direction and a proximal direction relative to a curved lumen of a patient, and wherein each of the strut elements has a portion extending to the proximal end of the introducer, wherein each strut is separately moveable to provide both pulling and pushing forces against the first end.

13. The introducer system of claim 12, wherein the plurality of strut elements comprises a first strut element and a second strut element, the first strut element releasably coupled to a first region of the first end of the implantable device associated with an outside part of the curved lumen of the patient, and the second strut element releasably coupled to a second region of the first end of the implantable device associated with an inside part of the curved lumen of the patient.

14. The introducer system of claim 12, wherein each of the strut elements further comprises a distal member fixed to the carrier element and a proximal member slidably engaged with the distal member, wherein, in response to movement of the proximal member, the distal member moves in either the proximal or distal direction to move respective regions of the first end of the implantable medical device in a direction corresponding to the respective direction of movement of the proximal member.

15. An introducer system for fitting an implantable medical device into a lumen of a patient, comprising:

the implantable medical device having a first end and a second end;

and an introducer comprising a flexible carrier element configured to carry the implantable medical device on the flexible carrier element, the flexible carrier element including a distal end having a nose cone attached thereto, a distal portion proximal of the nose cone at which the implantable medical device is located, and a plurality of substantially rigid strut elements fixedly connected to a proximal end of the nose cone or to the flexible carrier element adjacent the nose cone and arranged radially around the carrier element and releasably coupling the distal end of the carrier element to different attachment regions of the first end of the implantable medical device, each of the strut elements having sufficient rigidity to provide both a pulling and pushing force to the same end of the implantable medical device, wherein each strut element is separately movable to provide both the pulling and pushing force to the same end of the implantable medical device; and wherein, in response to pushing and pulling movement of a respective strut element in a distal direction and a proximal direction, respectively, the corresponding attachment region of the first end moves in a direction similar to the direction of movement of the respective strut element to position the first end relative to lumen of a patient at a desired relative position.

16. The introducer system of claim 15, wherein the desired relative position of the first end of the implantable medical device is substantially perpendicular to the lumen.

17. The introducer system of claim 15, wherein each of the strut elements comprises a relative stiffness configured to provide both pulling and pushing forces against a first region of the first end of the implantable medical device associated with a first part of the lumen, and to provide both of pulling and pushing forces against a second region, different than the first region, of the first end of the implantable medical device associated with a second part of the lumen.

* * * * *